United States Patent [19]
Dias et al.

[11] Patent Number: 5,827,181
[45] Date of Patent: Oct. 27, 1998

[54] NONINVASIVE BLOOD CHEMISTRY MEASUREMENT METHOD AND SYSTEM

[75] Inventors: J. Fleming Dias, Palo Alto; Ganapati R. Mauze, Sunnyvale, both of Calif.

[73] Assignee: Hewlett-Packard Co., Palo Alto, Calif.

[21] Appl. No.: 813,733

[22] Filed: Mar. 7, 1997

Related U.S. Application Data

[63] Continuation of Ser. No. 526,127, Sep. 7, 1995, abandoned.

[51] Int. Cl.⁶ .......................................................... A61B 5/00
[52] U.S. Cl. ............................ 600/322; 600/323; 600/335
[58] Field of Search ....................................... 600/310–342; 356/35.5

[56] References Cited

U.S. PATENT DOCUMENTS

| | | | |
|---|---|---|---|
| 4,425,039 | 1/1984 | Grant | 356/35.5 |
| 4,537,197 | 8/1985 | Hulka | 600/338 |
| 4,682,892 | 7/1987 | Chawla | 356/35.5 |
| 4,702,594 | 10/1987 | Grant | 356/35.5 |
| 4,883,055 | 11/1989 | Merrick | 600/335 |
| 4,938,218 | 7/1990 | Goodman et al. | 600/338 |
| 4,975,581 | 12/1990 | Robinson et al. . | |
| 5,054,487 | 10/1991 | Clarke . | |
| 5,070,874 | 12/1991 | Barnes et al. . | |
| 5,086,229 | 2/1992 | Rosenthal et al. . | |
| 5,247,932 | 9/1993 | Chung et al. | 600/338 |
| 5,424,545 | 6/1995 | Block et al. . | |

FOREIGN PATENT DOCUMENTS 0160768   5/1984   European Pat. Off. .

OTHER PUBLICATIONS

Reverse Iontophoresis: Development of a Noninvasive Approach for Glucose Monitoring; Girish Rao, Peretz Glikfeld and Richard H. Guy; Pharmaceutical Research, vol. 10, No. 12, 1993.

New Noninvasive Transcutaneous Approach to Blood Glucose Monitoring: Successful Glucose Monitoring on Human 75 g OGTT with Novel Sampling Chamber; Kayashima, Arai, Kikuchi, Sato, Nagata, Takatani, Ito, Kimura, Kuriyama, Kaneyoshi; IEEE Transactions on Biomedical Engineering, vol. 38, No. 8, No. 8, Aug. 1991.

Determination of Physiological Levels of Glucose in an Aqueous Matrix with Digitally Filtered Fourier Transform Near–Infrared Spectra; Mark A. Arnold and Gary W. Small; Dept. of Chemistry, The University of Iowa, Iowa City, Iowa 52242; Analytical Chemistry, vol. 62, No. 14, Jul. 15, 1990.

*Primary Examiner*—Robert L. Nasser
*Attorney, Agent, or Firm*—John L. Imperato

[57] ABSTRACT

A noninvasive blood chemistry measurement method and system isolate measurement contributions due to a patient's blood to accurately measure blood chemistry. In accordance with a first preferred embodiment of the present invention a noninvasive blood chemistry measurement method decreases the blood volume within a patient's body part relative to the normal blood volume in the body part and performs a baseline measurement. Blood volume is then increased and a second measurement is performed. Comparison of the second measurement to the baseline measurement isolates the measurement attributes of the patient's blood. In accordance with a second preferred embodiment of the present invention a noninvasive blood chemistry measurement system decreases blood volume by applying mechanical pressure to a body part. In accordance with a third preferred embodiment of the present invention, blood volume in the body part is decreased using a pressure cuff. In a fourth embodiment, a noninvasive probe accurately measures blood chemistry and uses a suction cup to increase blood volume at the blood chemistry measurement site.

1 Claim, 4 Drawing Sheets

NONINVASIVE BLOOD CHEMISTRY MEASUREMENT METHOD AND SYSTEM

CROSS REFERENCE TO RELATED APPLICATION(S)

This is a continuation of application Ser. No. 08/526,127 filed on Sep. 7, 1995, now abandoned.

FIELD OF THE INVENTION

The present invention relates to a method and system for noninvasively measuring blood chemistry.

BACKGROUND OF THE INVENTION

A patient's blood chemistry is often measured as a vital indicator of the patient's physiological condition and health. Traditionally, blood chemistry has been measured by extracting blood from the patient and then analyzing the extracted blood. Although this type of measurement is accurate, it is invasive and expensive, often requiring administration by trained medical personnel. Fortunately, various noninvasive interactions with the blood are also used to measure a patient's blood chemistry. For example, absorption or scattering of light by a part of a patient's body allows blood chemistry to be measured without extracting blood from the patient. Iontophoresis and other transcutaneous techniques that migrate analytes through the skin also show promise for noninvasive blood chemistry measurement.

A prior art noninvasive measurement method and apparatus are taught by Robinson et al., U.S. Pat. No. 4,975,581, which issued Dec. 4, 1990. Robinson et al. measure optical absorption by a patient's finger and then compare the similarity of the measurement to a data model constructed from measurements of biological fluids having known concentrations of analytes. The concentration of analytes in the finger is then determined from the comparison.

Another prior art noninvasive measurement system is taught by Clarke in U.S. Pat. No. 5,054,487 which issued Oct. 8, 1991. Clarke measures optical scattering to determine the concentration of analytes, such as glucose and cholesterol in a patient's blood, by measuring the ratio of the intensities of incident to the scattered light from a body part and comparing the measurements to predetermined values. Barnes et al. in U.S. Pat. No. 5,070,874, which issued Dec. 10, 1991 and Rosenthal et al. in U.S. Pat. No. 5,086,229, which issued Feb. 4, 1992, measure transmission of near infrared radiation through a body part and then analyze the measured data to determine glucose concentration.

Unfortunately, factors such as the patient's level of hydration and body temperature and the presence of bone, cartilage and collagen influence these optical and near infrared radiation measurements, but the factors do not correspond directly to the patient's blood chemistry. Since these factors are difficult to account for in data models and data analysis relied upon, they contribute errors to the blood chemistry measurements. As blood chemistry is a vital indicator of the physiological condition and health of a patient, it is important that any method or apparatus used to measure blood chemistry is accurate.

SUMMARY OF THE INVENTION

In accordance with a first illustrated preferred embodiment of the present invention a noninvasive blood chemistry measurement method isolates measurement attributes of a patient's blood. Isolating the measurement attributes of the blood reduces the influence of factors not corresponding to blood chemistry and enhances the accuracy of noninvasive blood chemistry measurements. Blood volume within a patient's body part is decreased relative to normal blood volume in the body part and a baseline measurement, such as an optical transmission or optical scattering measurement, is performed. The blood volume is then increased and a second measurement is performed. The measurements are compared and the difference between the measurements is primarily due to the change in blood volume. This difference isolates the measurement attributes of the patient's blood.

In accordance with a second illustrated preferred embodiment of the present invention a noninvasive blood chemistry measurement system applies mechanical pressure to decrease blood volume in a patient's finger and then a baseline measurement is performed. In accordance with a third illustrated preferred embodiment of the present invention blood volume in the patient's finger is reduced using a pressure cuff. In a fourth embodiment, a noninvasive probe uses a suction cup to increase blood volume at a blood chemistry measurement site while a second measurement is performed.

DETAILED DESCRIPTION OF THE PREFERRED EMBODIMENT

Figure 1:
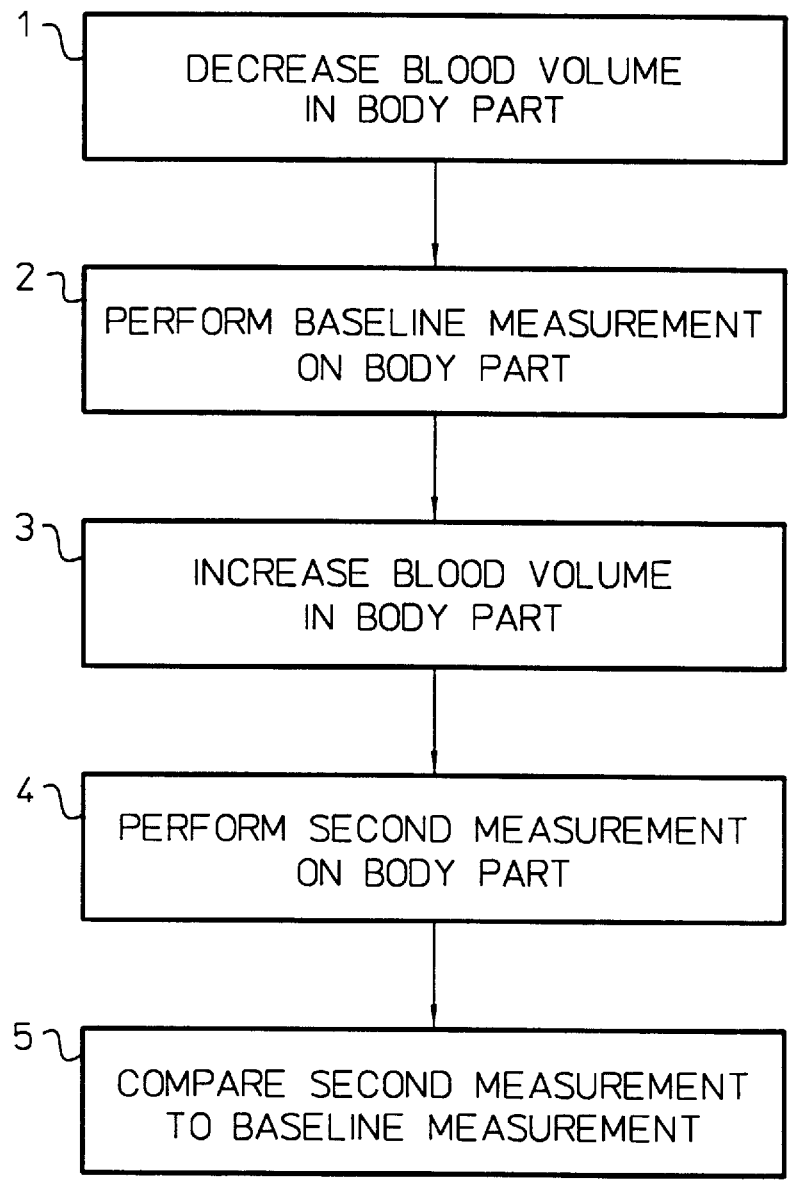
FIG. 1 shows a flow diagram of a noninvasive blood chemistry measurement method that is constructed in accordance with a first preferred embodiment of the present invention.

FIG. 1 shows a flow diagram of a noninvasive blood chemistry measurement method that is constructed in accordance with the first preferred embodiment of the present invention. In the first step 1 of the method the blood volume in a body part, such as a finger, toe or ear lobe, is decreased relative to the patient's normal blood volume in that body part. This is done by applying pressure to the body part. An example of decreasing the blood volume in the finger may be seen by pinching the finger and observing the finger as it turns from a red, blood-rich color to a white, blood-deprived color.

Once the blood volume in the body part is decreased a baseline measurement step 2 is performed. The baseline measurement may comprise a variety of noninvasive interactions with a patient's body part that correspond to the patient's blood chemistry. Examples of such noninvasive interactions are optical or light based interactions, electrical, magnetic, or acoustical interactions, or iontophoresis or other transcutaneous techniques. One type of noninvasive interaction suitable for the baseline measurement step 2 is taught by Robinson et al. in U.S. Pat. No. 4,975,581. Robinson et al. teach illuminating a portion of the body with light of predetermined wavelengths. Absorption of the light by the body at several wavelengths is then measured. However, instead of performing a baseline measurement at decreased blood volume in the body part, Robinson et al. compare the optical measurement to a calibration model to determine blood chemistry.

In the present invention, the blood volume in the body part is then increased as shown in step 3. The increase in blood volume constitutes a return to the normal blood volume, as it would be, for example, if pressure previously applied to the body part were removed, or more blood than normal is drawn by applying a partial vacuum to the body part. The increase in blood volume due to the partial vacuum is analogous to the reddening of a finger as a result of sucking on it.

Once the blood volume is increased, a second measurement step 4 is performed on the body part. The second measurement step 4 is identical to the baseline measurement step 2 with the exception that during the second measurement step 4 the body part has a higher blood volume than it had during the baseline measurement step 2.

The baseline measurement and the second measurement are then compared in step 5. The difference between the two measurements is primarily due to the change in blood volume in the body part. This difference isolates the measurement attributes of the patient's blood. Once isolated, the measurement attributes of the blood are used to accurately determine the patient's blood chemistry by comparing the difference between the baseline and second measurements to a simple calibration model based on measurements of blood samples. This noninvasive blood chemistry measurement method is more accurate than prior art methods which do not perform a baseline measurement but rather, use predetermined data or a calibration model as a basis for comparison. In the method of the present invention, errors that are caused by factors not related to the patient's blood chemistry may be eliminated by subtraction since they are present in the baseline and the second measurements. For example, the patient's body temperature, tissue hydration and the presence of bone, cartilage and collagen each effect optical measurements of the patient's body, but these factors do not correspond directly to the patient's blood chemistry. Comparison of the second measurement to the baseline measurement enables these sources of error to be eliminated.

Figure 2A:
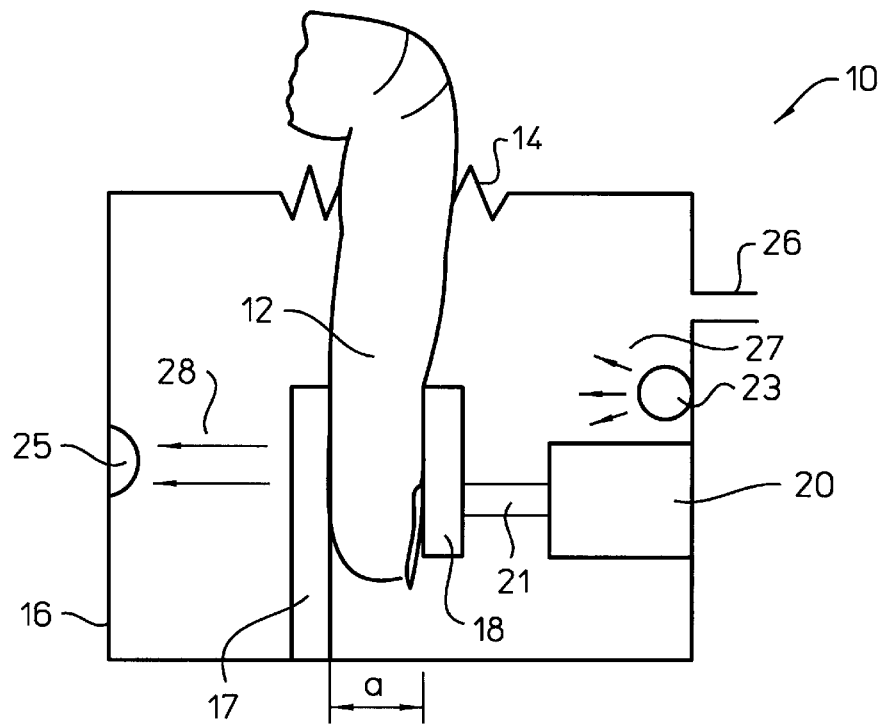
FIG. 2A and 2B show a cross-sectional view of a noninvasive blood chemistry measurement system that is constructed in accordance with a second preferred embodiment of the present invention.

FIG. 2A shows a cross-sectional view of a noninvasive blood chemistry measurement system 10 that is constructed according to the second preferred embodiment of the present invention. A body part such as a finger 12 is inserted through a seal 14 and into a chamber 16 which may be constructed from metal, plastic, or any other suitable material. Once the finger 12 is inserted, it rests against an optically transparent stop 17. A force is then applied by a linear actuator 20 to a sliding shaft 21 that is connected to an optically transparent plate 18 located on an opposite side of the finger 12 from the stop 17. The plate presses against the finger, pinching it between the plate 18 and the stop 17. Electro-mechanical, mechanical, pneumatic or other means may be used to move the plate 18.

At a first distance a from the stop 17, the plate 18 applies positive pressure to the finger 12, decreasing the blood volume in the finger 12. If the pressure exceeds the patient's systolic blood pressure, a large percentage of the blood is evacuated from the blood vessels in the finger 12. A baseline optical transmission measurement is then made on the finger 12 using incident light 27 from a light source 23. The incident light 27 travels through the plate 18, stop 17 and finger 12. A portion of the incident light 27 is absorbed by the finger 12 and other elements in the light path between the source 23 and a sensor 25. The incident light 27 not absorbed emerges as transmitted light 28 and is intercepted by the sensor 25. The ratio of intensity of the incident light 27 to the intensity of the transmitted light 28 establishes the baseline optical transmission measurement. The sensor 25 converts the transmitted light 28 into an electrical signal which may be recorded in the system electronics (not shown).

Figure 2B:
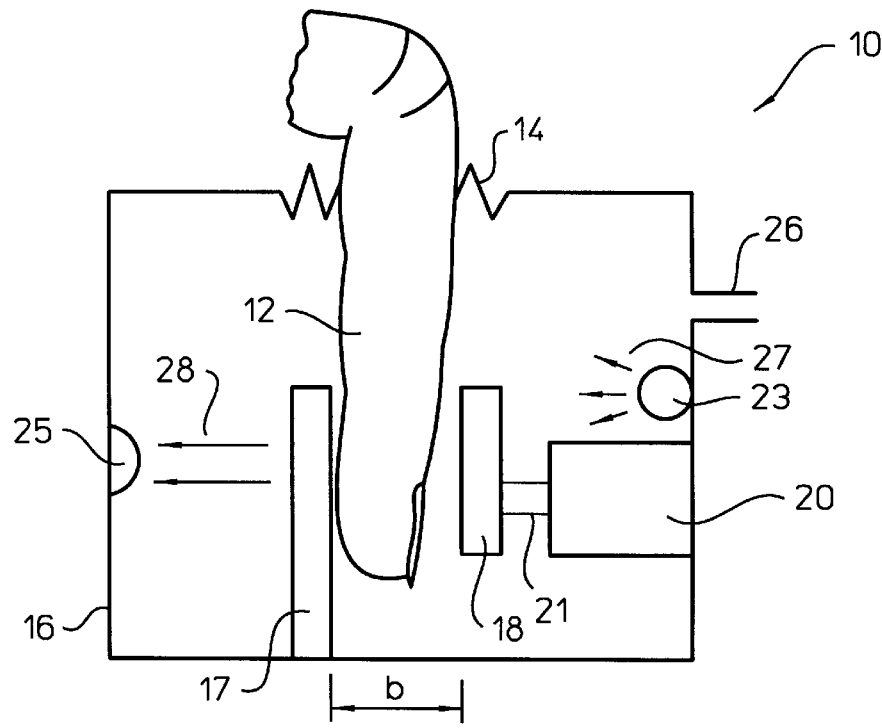

FIG. 2B shows the plate 18 positioned at a second distance b from the stop 17 such that the plate 18 no longer applies pressure to the finger 12. Blood then flows in the finger 12 and the blood volume in the finger returns to its normal volume. At this point, a second optical transmission measurement is performed. The second optical transmission measurement is performed identically to the baseline optical transmission measurement except that during the second optical transmission measurement, the finger 12 has a higher blood volume than it had during the baseline measurement. Since the conditions under which the two measurements are made differ primarily in the blood volume in the finger 12, the optical transmission of the blood is isolated by taking the difference between the second and baseline optical transmission measurements. Once the optical transmission of the blood is isolated, known techniques such as those taught by Robinson et al. in U.S. Pat. No. 4,975,581 may be used to compare the optical transmission of the blood to data established from blood samples having known chemical concentrations to accurately determine the patient's blood chemistry.

To further isolate the optical attributes of the patient's blood, the blood volume in the finger 12 may be further increased, relative to the normal volume before the second optical transmission measurement is performed. Pumping air out of the chamber 16 through a spout 26 establishes a partial vacuum in the chamber 16, reducing the pressure on the finger 12, which in turn decreases impedance to blood flow and causes the blood vessels in the finger 12 to fill. This causes the blood volume in the finger 12 to increase relative to the normal volume.

Figure 3A:
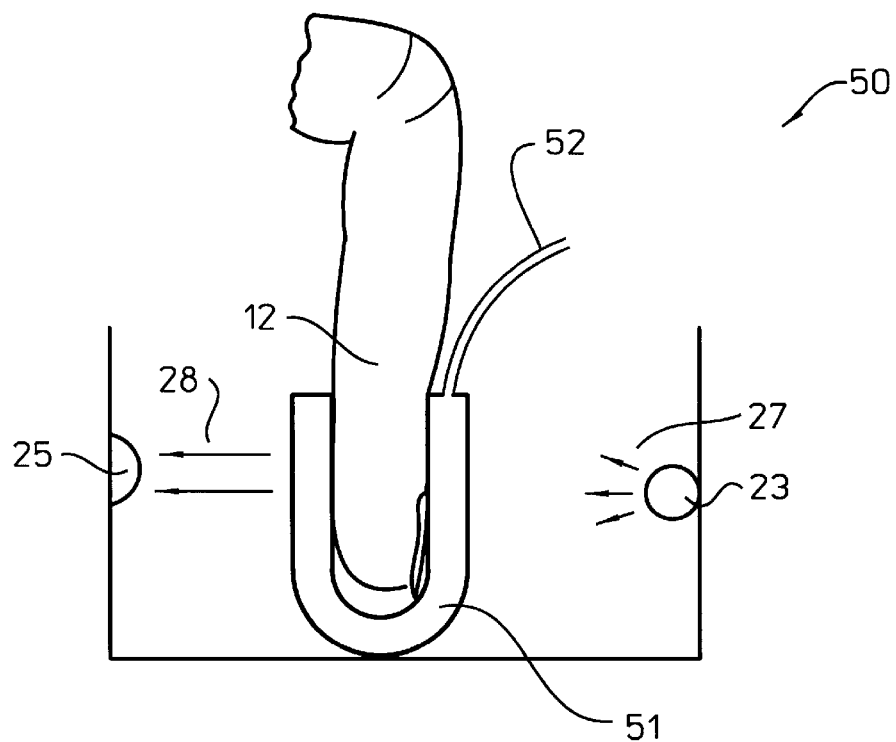
FIG. 3A and 3B show a cross-sectional view of a noninvasive blood chemistry measurement system including a cuff that is constructed in accordance with a third preferred embodiment of the present invention.

FIG. 3A shows a cross-sectional view of a noninvasive blood chemistry measurement system 50 including a cuff 51 that is constructed in accordance to a third preferred embodiment of the present invention. In this embodiment, an optically transparent cuff 51 applies positive pressure to a finger 12. When air is forced into the cuff 51 through a tube 52, the cuff inflates, applying pressure to the finger 12 and decreasing the blood volume in the finger. A baseline optical transmission measurement is performed with the cuff 51 in the inflated mode. An optical index matching fluid may be used instead of air to fill the cuff 51 in order to optimize the optical performance of the noninvasive measurement system 50. Incident light 27 travels from light source 23 through the cuff 51 and finger 12 and the transmitted light 28 is intercepted by the sensor 25. The sensor 25 converts the transmitted light signal 28 into an electrical signal which may be recorded by the system electronics (not shown).

Figure 3B:
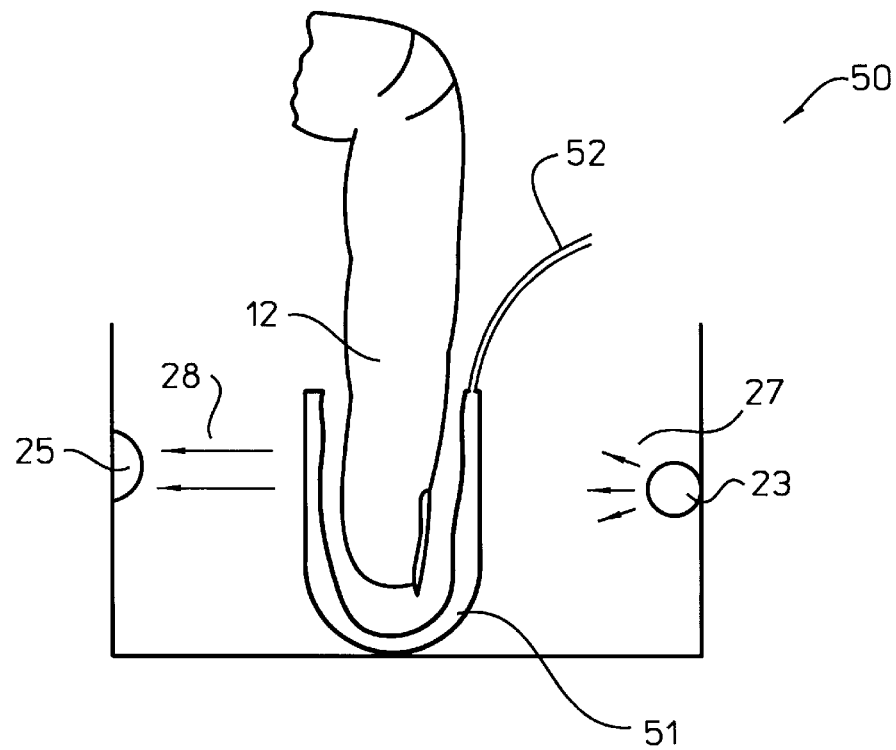

The cuff 51 is then deflated as shown in FIG. 3B by removing air or the index matching fluid from the cuff 51 through the tube 52. This relieves the pressure from the finger 12 and causes blood to flow back into the finger 12, returning the blood volume to its normal volume. Then a second optical transmission measurement is performed using the light source 23 and the sensor 25. Comparison of the baseline and second optical transmission measurement isolates the optical transmission of the blood. Known techniques are then applied to the isolated optical transmission of the blood to accurately determine a patient's blood chemistry. Factors that are not related to the blood chemistry, but which do influence the optical transmission measurements, are greatly reduced by comparing or by subtracting the measurements, since these factors contribute equally to the baseline and second optical transmission measurements.

As alternative embodiments of the second and third preferred embodiments of the present invention, optical scattering by a body part is measured to determine blood chemistry. For optical scattering measurements, the sensor 25 and the source 23 are located on the same side of the finger 12. The blood volume in the finger 12 is decreased relative to the normal blood volume and a baseline optical scattering measurement is performed on the incident light 27 scattered by the finger 12. The blood volume in the finger 12 is then increased and a second optical scattering measurement is performed. Optical scattering by the blood is isolated by comparing or subtracting the baseline and second optical scattering measurements. Once the optical scattering by the blood is isolated, a known method such as that taught by Clarke in U.S. Pat. No. 5,054,487 may be applied to the difference between the baseline and second optical measurements to determine the blood chemistry. Clarke determines the concentration of analytes, such as glucose and cholesterol in a patient's blood, by measuring the ratio of the intensities of incident to the scattered light from a body part.

Figure 4:
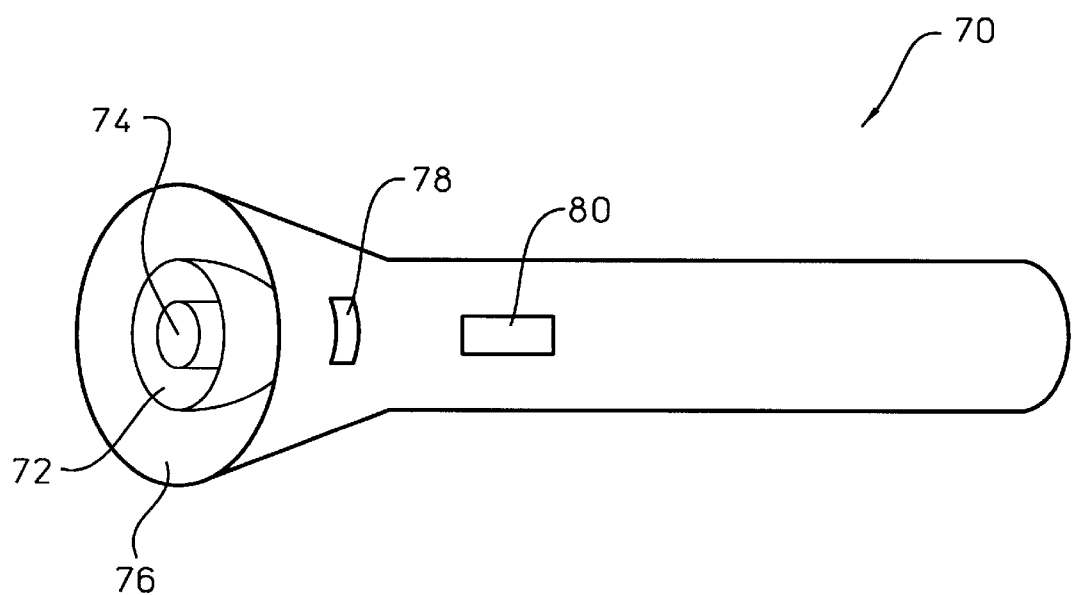
FIG. 4 shows a perspective view of a noninvasive blood chemistry measurement probe that is constructed in accordance with a fourth preferred embodiment of the present invention.

FIG. 4 shows a perspective view of a noninvasive blood chemistry measurement probe 70 that is constructed according to a fourth preferred embodiment of the present invention. The probe 70 has an open-ended suction cup 72 used to increase blood volume in a body part such as a patient's arm. An optical fiber bundle 74 is incorporated in the probe 70. To use the probe 70, it is positioned with the suction cup 72 and optical fiber bundle 74 contacting a patient's skin with the suction cup 72 forming an airtight seal at the interface to the skin.

A baseline optical scattering measurement is then performed. The fiber bundle 74 carries incident light from a light source (not shown) to the patient's skin. The light incident on the patient is partially absorbed and partially scattered. Scattered light is also intercepted by the fiber bundle 74 where it propagates to a light sensor (not shown). The ratio of the intensities of the scattered light to the incident light is recorded in the system electronics (not shown) providing the baseline optical scattering measurement. A vacuum is then applied to the suction cup 72. This draws blood to the region sealed by the suction cup 72 and the patient's skin, as it would be, for example, if one were to place the mouth on the arm and by suction draw blood to the area. Once blood is drawn to the region, a second optical scattering measurement is performed. The difference between the baseline optical scattering measurement and the second optical scattering measurement is due to the change in blood volume in the region of the body at which the optical scattering measurement is performed thus isolating optical scattering by the patient's blood. Once the optical scattering measurement due to the blood is isolated, a method such as that taught by Clarke in U.S. Pat. No. 5,054,487 may be used to establish the concentration of analytes in the blood.

For portable measurement applications, a housing 76 of the probe 70 contains a digital readout 78 to display blood chemistry readings and an activation switch 80 to enable the noninvasive blood chemistry measurements. Alternatively, the probe 70 may be connected to a remote measurement system through a system cable (not shown).

The noninvasive blood chemistry measurement systems in the preferred embodiments of the present invention isolate optical characteristics of the blood, such as optical transmission and optical scattering by performing measurements on a body part at different blood volumes. However, the present invention is also applicable to other noninvasive interactions with a body part to determine a patient's blood chemistry. For example, iontophoresis is a noninvasive interaction with a body part that uses an applied electrical potential to enhance the transport of both charged and neutral analytes, such as glucose, through a patient's skin. Iontophoresis may be used in conjunction with the noninvasive blood chemistry measurement method and systems taught by the present invention. Using iontophoresis, analytes transported across the skin are detected when the blood volume is decreased to establish a baseline measurement. Then, the analytes are detected at increased blood volume to establish a second measurement. The difference between the two measurements isolates the measurement attributes of the blood. Once the attributes of the blood are isolated, the patient's blood chemistry is noninvasively determined by measuring the analytes transported across the skin.

We claim:

1. An apparatus for isolating measurement attributes of blood in a human body part for a noninvasive blood chemistry measurement, comprising:

a light source for illuminating the body part;

a light sensor for receiving light transmitted through the body part and for converting the received light into an electrical signal;

means for applying positive pressure to the body part for decreasing blood volume in the body part; wherein the means for applying positive pressure includes a transparent plate positioned on one side of the body part, a transparent stop positioned on an opposite side of the body part and means for varying the distance between the plate and the stop; and means for applying negative pressure to the body part for increasing blood volume in the body part.

* * * * *